United States Patent [19]

Atwal et al.

[11] Patent Number: 5,310,932

[45] Date of Patent: May 10, 1994

[54] CHROMANYL SUBSTITUTED INDOLE POTASSIUM CHANNEL OPENERS

[75] Inventors: Karnail Atwal, Newtown, Pa.;
 George C. Rovnyak, Hopewell, N.J.

[73] Assignee: E. R. Squibb & Sons, Inc., Princeton, N.J.

[21] Appl. No.: 760,030

[22] Filed: Sep. 11, 1991

Related U.S. Application Data

[63] Continuation-in-part of Ser. No. 685,323, Apr. 15, 1991, abandoned.

[51] Int. Cl.$^5$ ............................................. C07D 405/04
[52] U.S. Cl. ..................................... 548/454; 548/411; 548/414; 546/167; 546/164
[58] Field of Search ....................... 548/454, 411, 414

[56] References Cited

U.S. PATENT DOCUMENTS 4,988,723  1/1991  Shiokawa et al. .................. 514/392

FOREIGN PATENT DOCUMENTS 0205292  12/1986  European Pat. Off. .
0214818   3/1987  European Pat. Off. .
0274821   7/1988  European Pat. Off. .
0344747  12/1989  European Pat. Off. .
0314446   6/1990  European Pat. Off. .
WO8707607 12/1987  PCT Int'l Appl. .

OTHER PUBLICATIONS

V. A. Ashwood et al., "Synthesis and Antihypertensive Activity of 4-(Cyclic amido)-2H-benzopyrans", *J. Med. Chem.*, 1986, 29, 2194–2201.

*Primary Examiner*—David B. Springer
*Attorney, Agent, or Firm*—Theodore R. Furman, Jr.; Ellen K. Park

[57] ABSTRACT

Novel compounds are disclosed having the formula

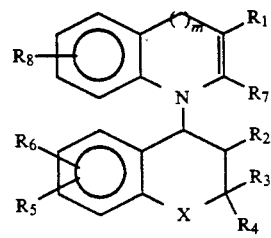

wherein X, $R_1$, $R_2$, $R_3$, $R_4$, $R_5$, $R_6$, $R_7$ and $R_8$ are as defined herein.

7 Claims, No Drawings

CHROMANYL SUBSTITUTED INDOLE POTASSIUM CHANNEL OPENERS

This is a continuation-in-part of U.S. Ser. No. 685,323 filed Apr. 15, 1991, abandoned.

FIELD OF THE INVENTION

The present invention relates to novel compounds having potassium channel activating activity which are therefore useful, for example, as cardiovascular agents.

SUMMARY OF THE INVENTION

In accordance with the present invention novel compounds having potassium channel activating activity which are useful, for example, as cardiovascular agents, are disclosed. These compounds have the general formula

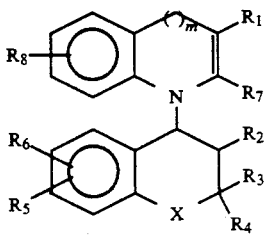

I wherein
X is —O—

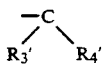

or a single bond;

$R_1$ and $R_7$ are independently selected from H, alkyl, haloalkyl, cycloalkyl, arylalkyl, CN, $NO_2$, COR, COOR, CONHR, $CONR_2$, halo wherein R in each of the above groups can be hydrogen, alkyl, haloalkyl, aryl, arylalkyl, cycloalkyl, or (cycloalkyl)alkyl;

$R_2$ is hydrogen, hydroxy,

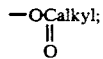

$R_3$, $R_3'$, $R_4$ and $R_4'$ are each independently selected from hydrogen, alkyl or arylalkyl, or, $R_3$ and $R_4$ (or $R_3'$ and $R_4'$) taken together with the carbon atom to which they are attached form a 5- to 7-membered ring; with the proviso that if $R_3$ and/or $R_4$ are other than hydrogen, then $R_3'$ and $R_4'$ are each hydrogen;

$R_5$ is hydrogen, alkyl, haloalkyl, alkenyl, alkynyl, cycloalkyl, arylalkyl, (cycloalkyl)alkyl, —CN, —$NO_2$, —COR, —COOR, —CONHR, —$CONR_2$, —$CF_3$, S-alkyl, —SOalkyl, —$SO_2$alkyl,

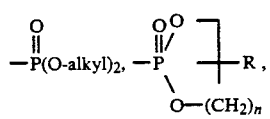

halogen, amino, substituted amino, O-alkyl, $OCF_3$, $OCH_2CF_3$, —OCOalkyl, —OCONRalkyl, —NRCOalkyl and NRCOOalkyl, $NRCONR_2$ wherein R in each of the above groups can be hydrogen, alkyl, haloalkyl, aryl, arylalkyl, cycloalkyl, or (cycloalkyl)alkyl;

$R_6$ is selected from H, alkyl, OH, O-alkyl, amino, substituted amino, NHCOR, CN, and $NO_2$ wherein R can be hydrogen, alkyl, haloalkyl, aryl, arylalkyl, cycloalkyl, or (cycloalkyl)alkyl;

$R_8$ is H, alkyl, haloalkyl, cycloalkyl, O—R, CN, $NO_2$, $CF_3$, halo, S-alkyl, COR, COOR, NRCOalkyl, OCOalkyl wherein R in each of the above groups can be hydrogen, alkyl, haloalkyl, aryl, arylalkyl, cycloalkyl, or (cycloalkyl)alkyl;

m is 0, or 1; and
n is 1, 2 or 3.

DETAILED DESCRIPTION OF THE PRESENT INVENTION

This invention in its broadest aspects relates to the indole and dihydroquinoline derivatives of formula I above, to compositions and the methods of using such compounds. The compounds of formula I are useful, for example, as cardiovascular agents. Preferred compounds are those with the 4R stereochemistry and having either $R_1$ or $R_7$ as COR, COOR, CONHR, $CONR_2$ wherein R in each of the above groups can be hydrogen, alkyl, haloalkyl, aryl, arylalkyl, cycloalkyl, or (cycloalkyl)alkyl.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 4 to 7 carbon atoms with cyclopentyl and cyclohexyl being most preferred.

The term "halo" or "halogen" refers to chloro, bromo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —$N(alkyl)_2$ wherein alkyl is of 1 to 4 carbons, —$CF_3$, —$OCHF_2$,

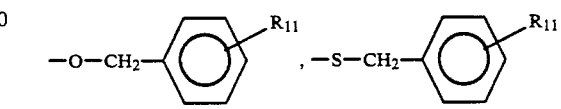

(wherein $R_{11}$ is hydrogen, alkyl of 1 to 4 carbons, alkoxy of 1 to 4 carbons, alkylthio of 1 to 4 carbons, halo, hydroxy or $CF_3$), —O—$CH_2$—cycloalkyl, or —S—$CH_2$— cycloalkyl, and di-substituted phenyl, 1- naphthyl, 2-naphthyl wherein said substituents are selected from methyl, methoxy, methylthio, halo, $CF_3$, nitro, amino, and $OCHF_2$.

Preferred aryl groups include unsubstituted phenyl and monosubstituted phenyl wherein the substituents are nitro, halo, —$CF_3$, alkyl, cyano or methoxy.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —N-H—alkyl wherein alkyl is of 1 to 4 carbons, —$N(alkyl)_2$ wherein alkyl is of 1 to 4 carbons, $CF_3$, or $OCHF_2$ or such monocyclic and bicyclic rings wherein two or three available carbons have substituents selected from methyl, methoxy, methylthio, halo, $CF_3$, nitro, hydroxy, amino and $OCHF_2$.

The term "substituted amino" refers to a group of the formula —$NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I wherein $R_2$ is hydroxy can be prepared by reacting a compound of the formula

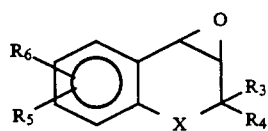

with a compound of the formula

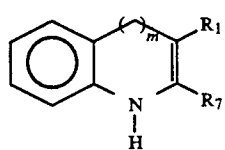

in a solvent, e.g., dimethylformamide, and in the presence of a base, e.g., potassium carbonate. In addition to the desired product I, one often obtains the olefin of the formula

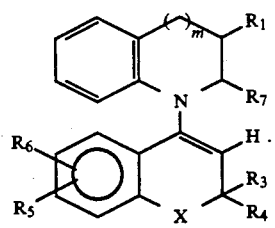

The epoxide of formula II where X is oxygen can be prepared by methods described in the literature, such as by J. M. Evans, C. S. Fake, T. C. Hamilton, R. H. Payser and E. A. Watts, *J. Med. Chem.*, 1983, 26, 1582 and *J. Med. Chem.*, 1986, 29, 2194; R. W. Lang, P. F. Wenk, *Helvetica Chimica Acta.*, 1988, 71, 596; EP 0,205,292 A2 (1986), and WO 87/07607.

The epoxide of formula II wherein X is $CH_2$ can be prepared using methodology described in EP 168-619-A.

Compounds of formula II where X is a single bond can be prepared using methodology described in EP 321-175 and by D. R. Buckle et al. in *J. Med. Chem.*, 1991, 34, 919.

Compounds of formula III are available from commercial sources or can be prepared by standard methods.

The compounds of the present invention where $R_2$ is other than hydroxy can be prepared by known techniques. For example, compounds wherein $R_2$ is OCOalkyl can be prepared by acylation of the alcohol of formula I, wherein $R_2$ is OH, with an acid chloride of the formula

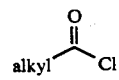

in the presence of a base catalyst, such as pyridine or triethylamine.

Compounds of formula I wherein $R_2$ is hydrogen can be prepared by catalytic hydrogenation of the olefin of formula IV.

Preferred compounds are those wherein
$R_1$ is —CN or —COOR;
$R_2$ is hydroxy or hydrogen;
$R_3$ and $R_4$ are each alkyl;
$R_4$ is an electron withdrawing group selected from CN, $NO_2$ or $CF_3$;
$R_6$ is hydrogen, alkyl, O-alkyl, amino;
$R_7$ is hydrogen or —COOR;
$R_8$ is hydrogen or halogen; and,
m is 0 or 1.

Most preferred are those compounds wherein
$R_1$ is —CN, H or —$COOCH_3$;
$R_2$ is trans-hydroxy;
$R_3$ and $R_4$ are each methyl;
$R_5$ is —CN or —$NO_2$;
$R_6$ is hydrogen;
$R_7$ is hydrogen or —$COOCH_3$;
$R_8$ is hydrogen; and,
m is 0.

The compounds of the present invention can have asymmetric centers at carbons 2–4 of benzopyran ring.

Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of formula I and the pharmaceutically acceptable salts act as potassium channel activators. Thus, compounds of the present invention are useful as anti-arrhythmic agents, and as antiischemic agents.

It has been found that compounds of formula I are particularly useful as antiischemic agents, i.e., for the treatment of ischemic conditions such as myocardial ischemia, cerebral ischemia, lower limb ischemia and the like. Unexpectedly, these compounds have been found to be "selective" antiischemic agents in that they possess little or no vasodilator activity in healthy tissue and have little or no effect on blood pressure. Therefore, this means that in the treatment of, for example, ischemic heart, these compounds are less likely to cause coronary steal, profound hypotension and coronary underperfusion. By little or no vasodilation activity is meant that these compounds have $IC_{50}$ (rat aorta) values greater than that of the potassium channel activator, cromakalim. The "selective" antiischemic agents typically are those having $IC_{50}$ (rat aorta) values >10 times that of cromakalim (i.e., have 1/10 the vasodilatory action) and preferably those having $IC_{50}$ values >50 times that of cromakalim.

Thus, by the administration of a composition containing one (or a combination) of the compounds of this invention ischemic conditions of a hypertensive mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenience delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, as well as for the promotion of hair growth (e.g., in the treatment of male pattern baldness) and as anti-asthmatic agents.

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice The amount of active substance in these compositions or preparations is such that a suitable dosage in the range indicated is obtained.

The present invention will now be described by the following examples, however, the invention should not be limited to the details therein.

EXAMPLE 1 trans-4-(3-Cyano-1H-indol-1-yl)-3,4-dihydro-3-hydroxy-2,2-dimethyl-2H-1-benzopyran-6-carbonitrile The reaction mixture containing 6-cyano-3,4-epoxy-3,4-dihydro-2,2-dimethyl-2H-benzopyran (1.5 g, 7.5 mmol) (prepared according to Evans et al., *J. Med. Chem.*, 1983, 26, 1582 and *J. Med. Chem.*, 1986, 29, 2194), 3-cyanoindole (1.46 g, 9.75 mmol) and finely ground potassium carbonate (2.6 g, 18.75 mmol) in dimethylformamide (5.0 mL) was heated at 100° C. for three hours. The reaction mixture was cooled to room temperature, diluted with ethyl acetate and filtered. The filtrate was washed with water, 1N hydrochloric acid, sodium bicarbonate solution and brine. After drying over anhydrous magnesium sulfate, the solvent was evaporated to yield a colorless solid. This material was purified by flash chromatography (20% ethyl acetate in hexanes) to yield 4-(3-cyano-1H-indol-1-yl)-2,2-dimethyl-2H-1-benzopyran-6-carbonitrile (1.45 g) as a colorless solid, m.p. 192°–193° C. (dichloromethaneisopropyl ether): $^1$H NMR (CDCl$_3$) δ 7.72 (m, 1 H), 7.6 (s, 1 H), 7.40 (dd, J=8.2 and 1.8 Hz, 1 H), 7.25 (m, 2 H), 7.1 (m, 1 H), 6.90 (d, J=8.7 Hz, 1 H), 6.70 (d, J=2.3 Hz, 1 H), 5.88 (s, 1 H), 1.55 (s, 6 H); $^{13}$C NMR (CDCl$_3$) 156.8, 135.6, 135.3, 134.9, 134.4, 129.9, 129.5, 127.3, 126.6, 124.8, 123.0, 120.1, 119.0, 118.2, 114.8, 111.3, 104.5, 88.7, 78.6, 27.9 ppm.

Analysis Calc'd for $C_{21}H_{15}N_3O$

C, 77.52; H, 4.65; N, 12.91;
Found: C, 77.35; H, 4.65; N, 12.82.

Further elution of the column provided the title compound (more polar) (110 mg), m.p. 175°–180° C: H$^1$NMR (CDCl$_3$) δ 7.9–6.5 (complex m, 8 H), 5.6, 5.2 (doublets, J=8 Hz, 1 H), 4.15, 4.05 (br singlets, 1 H), 3.15, 3.05 (br singlets, 1 H), 1.45, 1.35 (singlets, 3 H each). The NMR shows doubling of signals due to two rotamers present in solution.

Analysis Calc'd for $C_{21}H_{17}N_3O_2.0.3\ H_2O$

C, 72.32; H, 5.09; N, 12.05;
Found: C, 72.56; H, 4.98; N, 11.81.

EXAMPLE 2 trans-1-(6-Cyano-3,4-dihydro-3-hydroxy-2,2-dimethyl-2H-1-benzopyran-4-yl)-1H-indole-2-carboxylic acid, methyl ester To a solution of 6-cyano-3,4-epoxy-3,4-dihydro-2,2-dimethyl-2H-benzopyran (2.0 g, 9.95 mmol) (prepared according to Evans et al., *J. Med. Chem.*, 1983, 26, 1582 and *J. Med. Chem.*, 1986, 29, 2194), and indole-2-carboxylic acid, ethyl ester (2.25 g, 11.9 mmol) in dimethylforamide (10.0 mL) at 0° C. under argon was added sodium hydride (476 mg of 60% oil dispersion, 11.92 mmol) in portions. After the addition was finished, the reaction mixture was allowed to warm up to room temperature and then heated at 90° C. for 16 hours. It was cooled to 0° C. in ice bath and diluted with ethyl acetate. To the resulting solution was added 1N hydrochloric acid until pH~5. The organic layer was separated and the aqueous layer was reextracted with ethyl acetate. The combined organic extracts were washed with water, brine and dried over anhydrous magnesium sulfate. The solvent was evaporated and the residue in dichloromethanemethanol (90:10) at 0° C. was treated with freshly prepared diazomethane. The reaction mixture was warmed up to room temperature and stirred for 1 hour. Few drops of acetic acid were added to decompose excess diazomethane (until reaction mixture turned colorless) and the solvent was evaporated to yield a brown oil It was purified by flash chromatography (dichloromethane) to yield the less polar 1-(6-cyano-2,2-dimethyl-2H-benzopyran-4-yl)-1H-indole-2-carboxylic acid, methyl ester (1.6 g). Further elution furnished the more polar title compound (380 mg) as a colorless solid, m.p. 197°–200° C. (isopropyl ether): IR (KBr) 2227, 1710, 1489, 1207 cm$^{-1}$; $^1$H NMR (DMSO-d$_6$) δ 7.7 (m, 2 H), 7.47, 7.41 (s, 1 H), 7.15 (m, 3 H), 7.0, 6 85 (d, J=10 Hz, 1 H), 6.6 (m, 1 H), 5.75 (d, J=5.8 Hz, 1 H), 4.5, 4.2 (m, 2 H), 3.9, 3.5 (s, 3 H), 1.48, 1.45 (s, 3 H), 1.37, 1.27 (s, 3 H) (doubling of signals due to rotamers present in solution); $^{13}$C NMR (DMSO-d$_6$) 162.1, 156.2, 136.3, 133.3, 131.9, 129.8, 126.9, 124.7, 123.4, 123.2, 120.6, 118.5, 112.5, 111.0, 103.3, 81.25, 68.84, 54.8, 51.9, 26.5, 18.25 ppm. The peaks due to the minor rotamer appear at 132.5, 125.2, 123.0, 122.3, 121.0, 117.8, 113.2, 71.4, 56.2, 51.6, 26.8, 22.8, 18.7 ppm.

Analysis Calc'd for $C_{22}H_{20}N_2O_4.0.2\ H_2O$

C, 69.49; H, 5.41; N, 7.37;
Found: C, 69.71; H, 5.44; N, 7.15.

EXAMPLE 3 trans-1-(6-Cyano-3,4-dihydro-3-hydroxy-2,2-dimethyl-2H-1-benzopyran-4-yl)-1H-indole-3-carboxylic acid, methyl ester To the solution of 6-cyano-3,4-epoxy-3,4-dihydro-2,2-dimethyl-2H-benzopyran (1.15 g, 5.71 mmol) (prepared according to Evans et al., *J. Med. Chem.*, 1983, 26, 1582 and *J. Med. Chem.*, 1986, 29, 2194), and indole-3-carboxylic acid, methyl ester (1.0 g, 5.71 mmol) in dimethylformamide (5.0 mL) under argon was added finely ground potassium carbonate (1.93 g, 14.0 mmol). The reaction mixture was heated at 90° C. for 4 hours and cooled to ambient temperature. It was diluted with ethyl acetate and filtered. The filtrate was washed with water, 10% citric acid, brine and dried over anhydrous magnesium sulfate. The solvent was evaporated to yield a colorless foam. It was purified by flash chromatography (5% ethyl acetate in hexanes) to give 1-(6-cyano-2,2-dimethyl-2H-1-benzopyran-4-yl)-1H-indole-3-carboxylic acid, methyl ester (990 mg), m.p. 177°–180° C. (ether-hexanes): $^1$H NMR (DMSO-d$_6$) δ 8.3 (s, 1 H), 8.21 (d, J=6.4 Hz, 1 H), 7.80 (dd, J=8.8 and 2.4 Hz, 1 H), 7.35 (m, 3 H), 7.18 (d, 8.2 Hz, 1 H), 6.90 (d, J=1.7 Hz, 1 H), 6.42 (s, 1 H), 3.93 (s, 3 H), 1.68 (s, 6 H); $^{13}$C NMR (DMSO-d$_6$) 164.5, 156 9, 136.9, 135.5, 135.2, 130.9, 128.7, 126.7, 126.3, 123.8, 122.7, 121.4, 119.8, 118.8, 118.4, 111.6, 108.4, 103.7, 79.3, 51.3, 27.9 ppm; IR (KBr) 2224, 1705, 1207 cm$^{-1}$.

Analysis Calc'd for $C_{22}H_{18}N_2O_3$

C, 73.73; H, 5.06; N, 7.82;
Found: C, 73.63; H, 5.00; N, 7.71.

Further elution of the column provided the more polar title compound, m.p. 211°–213° C. (iospropyl ether); IR (KBr): 2225, 1693, 1537, 1489 cm$^{-1}$.

Analysis Calc'd for $C_{22}H_{20}N_2O_4$

C, 70.20; H, 5.36; N, 7.44;
Found: C, 70.27; H, 5.38; N, 7.36.
The $^1$H NMR and $^{13}$C NMR show this compound to be a mixture of rotamers.

EXAMPLE 4

1-(6-Cyano-3,4-dihydro-2,2-dimethyl-2H-1-benzopyran-4-yl)-1H-indole-3-carbonitrile 4-(3-Cyano-1H-indol-1-yl)-2,2-dimethyl-2H-1-benzopyran-6-carbonitrile (25 mg, prepared according to Example 1) in methanol/ethyl acetate (3:1) was treated with an equal weight of palladium hydroxide catalyst and shaken under an atmosphere of hydrogen at 55 psi over 2 days, recharging the catalyst midway, to provide a 53:30 mixture of the desired compound and the starting material along with minor amounts of by-products. Another 250 mg of starting material was treated in an identical manner. Purification of the desired product from the combined reaction mixtures was effected by preparative reverse phase chromatography on a C-18 column, eluting with 85% of 90:10 MeOH:H$_2$O with 0.1% trifluoroacetic acid and 15% of 10:90 MeOH:H$_2$O with 0.1% trifluoroacetic acid at a flow rate of 49 mL/min. and injections of 75 mg. Product-containing fractions were concentrated to remove methanol and extracted twice with ethyl acetate. The organic extracts were washed with saturated sodium bicarbonate, water and brine, dried over anhydrous magnesium sulfate and concentrated in vacuo to give a residue of 50 mg. Final hexane trituration (decanted) gave the title compound (45 mg), m.p. 175°–178° C.: $^1$H NMR (CDCl$_3$) δ 7.80–7.88 (m, 1H), 7.48–7.65 (m, 2H), 7.25–7.40 (m, 2H), 7.10–7.30 (m, 1H), 6.95–7.05 (m, 2H); $^{13}$C NMR (CDCl$_3$) δ 157.8, 134.0, 133.8, 133.7, 133.6, 132.2, 124.7, 123.1, 120.8, 120.7, 119.6, 118.6, 115.4, 111.0, 110.9, 104.3, 77.4, 51.0, 39.4, 29.7, 24.7.

Analysis Calc'd for C$_{21}$H$_{17}$N$_3$O.0.25 H$_2$O
C, 75.98; H, 5.32; N, 12.66;
Found: C, 76.22; H, 5.19; N, 12.42.

What is claimed is:

1. A compound of the formula

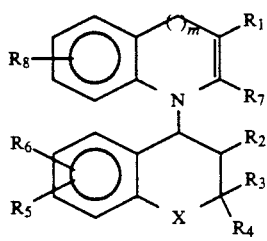

I wherein X is —O—;

R$_1$ and R$_7$ are independently selected from H, alkyl, haloalkyl, cycloalkyl, arylalkyl, CN, NO$_2$, COR, COOR, CONHR, CONR$_2$, halo wherein R in each of the above groups can be hydrogen, alkyl, haloalkyl, aryl, arylalkyl, cycloalkyl, or (cycloalkyl)alkyl where at least one of R$_1$ or R$_7$ is H;

R$_2$ is hydrogen, hydroxy,

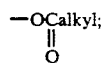

R$_3$ and R$_4$ are each independently selected from hydrogen, alkyl or arylalkyl, or, R$_3$ and R$_4$ taken together with the carbon atom to which they are attached form a 5- to 7-membered ring;

R$_5$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CONR$_2$, —CF$_3$, S-alkyl, —SOalkyl, —SO$_2$alkyl,

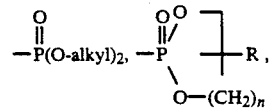

halogen, amino, substituted amino, O-alkyl, OCF$_3$, OCH$_2$CF$_3$, —OCOalkyl, —OCONRalkyl, —NRCOalkyl and NRCOOalkyl, NRCONR$_2$ wherein R in each of the above groups can be hydrogen, alkyl haloalkyl, aryl, arylalkyl, cycloalkyl, or (cycloalkyl)alkyl;

R$_6$ is selected from H, alkyl, OH, O-alkyl, amino, substituted amino, NHCOR, CN, and NO$_2$ wherein R can be hydrogen, alkyl, haloalkyl, aryl, arylalkyl, cycloalkyl, or (cycloalkyl)alkyl;

R$_8$ is H, alkyl, haloalkyl, cycloalkyl, O—R, CN, NO$_2$, CF$_3$, halo, S-alkyl, COR, COOR, NRCOalkyl, OCOalkyl wherein R in each of the above groups can be hydrogen, alkyl, haloalkyl, aryl, arylalkyl, cycloalkyl, or (cycloalkyl)alkyl;

m is 0; and n is 1, 2 or 3.

2. A compound in accordance with claim 1 wherein
R$_1$ is —CN or —COOR;
R$_2$ is hydroxy or hydrogen;
R$_3$ and R$_4$ are each alkyl;
R$_5$ is an electron withdrawing group selected from CN, NO$_2$ or CF$_3$;
R$_6$ is hydrogen, alkyl, O-alkyl, amino;
R$_7$ is hydrogen or —COOR;
R$_8$ is hydrogen or halogen; and
m is 0.

3. A compound in accordance with claim 1 wherein
R$_1$ is —CN, H or —COOCH$_3$;
R$_2$ is trans-hydroxy;
R$_3$ and R$_4$ are each methyl;
R$_5$ is —CN or —NO$_2$;
R$_6$ is hydrogen;
R$_7$ is hydrogen or —COOCH$_3$;
R$_8$ is hydrogen; and,
m is 0.

4. A compound in accordance with claim 1 having the name trans-4-(3-cyano-1H-indol-1-yl)-3,4-dihydro-3-hydroxy-2,2-dimethyl-2H-1-benzopyran-6-carbonitrile.

5. A compound in accordance with claim 1 having the name trans-1-(6-cyano-3,4-dihydro-3-hydroxy-2,2-dimethyl-2H-1-benzopyran-4-yl)-1H-indole-2-carboxylic acid, methyl ester.

6. A compound in accordance with claim 1 having the name trans-1-(6-cyano-3,4-dihydro-3-hydroxy-2,2-dimethyl-2H-1benzopyran-4-yl)-1H-indole-3-carboxylic acid, methyl ester.

7. A compound in accordance with claim 1 having the name 1-(6-cyano-3,4-dihydro-2,2-dimethyl-2H-1-benzopyran-4-yl)-1H-indole-3-carbonitrile.

* * * * *